United States Patent [19]
Cohen et al.

[11] Patent Number: 6,110,746
[45] Date of Patent: Aug. 29, 2000

[54] PEPTIDES DERIVED FROM HUMAN HEAT SHOCK PROTEIN 60 FOR TREATMENT OF DIABETES, COMPOSITIONS, METHODS AND KITS

[75] Inventors: Irun R. Cohen; Dana Elias, both of Rehovot; Rivka Abulafia, Yahud, all of Israel; Jana Bockova, Stony Brook, N.Y.

[73] Assignee: Yeda Research and Development Co. Ltd., Rehovot, Israel

[21] Appl. No.: 08/981,787

[22] PCT Filed: Jul. 1, 1996

[86] PCT No.: PCT/US96/11375

§ 371 Date: Apr. 27, 1998

§ 102(e) Date: Apr. 27, 1998

[87] PCT Pub. No.: WO97/01959

PCT Pub. Date: Jan. 23, 1997

[30] Foreign Application Priority Data

Jun. 30, 1995 [IL] Israel .................................. 114407

[51] Int. Cl.[7] ..................... G01N 33/564; G01N 33/536; C07K 7/08; C07K 14/00
[52] U.S. Cl. .......................... 436/506; 436/542; 530/350; 530/827; 530/868; 530/326
[58] Field of Search ................................... 435/7.92, 7.2, 435/7.8, 29; 436/506, 542; 514/2, 866; 530/350, 827, 868, 326

[56] References Cited

U.S. PATENT DOCUMENTS 4,976,958 12/1990 Shinnick et al. ........................... 424/92
5,242,823 9/1993 Fareed et al. ......................... 435/252.3

OTHER PUBLICATIONS

De Graeff–Meeder, ER et al. Pediatric Research 34 (4): 424–428, Apr. 1993.
Kilidireas, K et al The Lancet, 340 (8819): 569–572, Sep. 1992.
Lancet, vol. 343, Mar. 19, 1994. Elias et al., "Peptide therapy for diabetes in NOD mice", pp. 704–706.
The Journal of Immunology, vol. 153, No. 3, Aug. 1, 1994. Somoza et al., "Pancreas in recent onset insulin–dependent diabetes mellitus. Changes in HLA, adhesion molecules and autoantigens, restricted T cell receptor Vbeta usage, and cytokine profile", pp. 1360–1377.
Experientia, vol. 48, 1992. Yang et al., "Heat shock proteins in autoimmune disease. From causative antigen to specific therapy?", pp. 650–656.
Proc. Natl. Acad. Sci. USA, vol. 88, Apr. 1991. Elias et al., "Vaccination against autoimmune mouse diabetes with a T–cell epitope of the human 65–kDa heat shock protein", pp. 3088–3091.
JF. Bach. "Insulin–dependent diabetes mellitus as an autoimmune disease", Endocrine Reviews, vol. 15, No. 4, pp. 516–542, 1994.
A. Bendelac et al., "Syngeneic transfer of autoimmune diabetes from diabetic NOD mice to healthy neonates: Requirement for both L3T4[+] and Lyt–2[+] T cells", J.Exp. Med., vol. 166, pp. 823–832, Oct. 1987.
O. Birk, "NOD mouse diabetes: The Ubiquitous mouse Hsp60 is a β–cell target antigen of autoimmune T cells", Journal of Autoimmunity, vol. 9, pp. 159–166, 1996.
M. Bowman, "Prevention of diabetes in the NOD mouse: Implications for therapeutic intervention in human disease", Immunology Today, vol. 15, No. 3, pp. 115–120, 1994.
I. Cohen, "Autoimmunity to chaperonins in the pathogenesis of arthritis and diabetes", Annu. Rev. Immunol., vol. 9, pp. 567–589, 1991.
D. Elias et al., Treatment of autoimmune diabetes and insulitis in NOD mice with heat shock protein 60 peptide p277, Diabetes, vol. 44, pp. 1132–1138, Sep. 1995.
D. Elias et al., "The hsp60 peptide p277 arrests the autoimmune diabetes induced by the toxin streptozotocin" Diabetes, vol. 45, pp. 1168–1171, Sep. 1996.
J. Katz et al., "The helper cell subsets in insulin–dependent diabetes", Science, vol. 268, pp. 1185–1188, May 26, 1995.
D. Kaufman et al., "Spontaneous loss of T–cell tolerance to glutamic acid decarboxylase in murine insulin–dependent diabetes", Letter to Nature, vol. 366, pp.69–72, Nov. 4, 1993.
R. Tisch et al., "Immune response to glutamic acid decarboxylase correlates with insulitis in non–obese diabetic mice", Letter To Nature, vol. 366, pp. 72–75, Nov. 4, 1993.

*Primary Examiner*—Christina Y. Chan
*Assistant Examiner*—F. Pierre VanderVegt
*Attorney, Agent, or Firm*—Browdy and Neimark

[57] ABSTRACT

Novel peptides which are epitopes of the human 60 kDa heat shock protein (hsp60) may be used for the diagnosis and treatment of insulin-dependent diabetes mellitus (IDDM). Pharmaceutical compositions containing such peptides and kits for use in diagnosis of IDDM are also disclosed.

15 Claims, 8 Drawing Sheets

```
                                                          p3
  1    MLRLPTVTRQ  MRPVSRVLAP  HLTRAYANDV  KFGADARALM  LQGVDLLADA

51    VAVTMGPKGT  TVIIEQSWGS  PKVTKDGVTV  AKSIDLKDKY  KNIGAKLVQD p10
101    VANNTNEEAG  DGTTTATVLA  RSIAKEGFEK  ISKGANPVEI  RRGVMLAVDA p11              p12
151    VIAELKKQSK  PVTTPEEIAQ  VATISANGDK  EIGNIISDAM  KKVGRKGVIT p14
201    VKDGKTLNDE  LEIIEGMKED  RGYISPYFIN  TSKGQKCEFQ  DAYVLLSEKK p18          p19             p20
251    ISSIQSIVPA  LEIANAHRKP  LVIIAEDVDG  EALSTLVLNR  LKVGLQVVAV p21                                        p39
301    KAPGFGDNRK  NQLKDMAIAT  GGAVFGEEGL  TLNLEDVQPH  DLGKVGEVIV p24
351    TKDDAMLLKG  KGDKAQIEKR  IQEIIEQLDV  TTSEYEKEKL  NERLAKLSDG
                                                                p30
                                     p29            p277
401    VAVLKVGGTS  DVEVNEKKDR  VTDALNATRA  AVEEGIVLGG  GCALLRCIPA p278           p32
451    LDSLTPANED  QKIGIEIIKR  TLKIPAMTIA  KNAGVEGSLI  VEKIMQSSSE p35
501    VGYDAMAGDF  VNMVEKGIID  PTKVVRTALL  DAAGVASLLT  TAEVVVTEIP

551    KEEKDPGMGA  MGGMGGGMGG  GMF
```

PEPTIDES DERIVED FROM HUMAN HEAT SHOCK PROTEIN 60 FOR TREATMENT OF DIABETES, COMPOSITIONS, METHODS AND KITS

CROSS-REFERENCE TO RELATED APPLICATIONS

The present application is a 35 U.S.C. 371 national phase application of PCT/US96/11375, filed Jul. 1, 1996.

FIELD OF THE INVENTION

The present invention relates to novel peptides being epitopes of the human 60 KDa heat shock protein (hsp 60) and to pharmaceutical compositions comprising them for the diagnosis and treatment of insulin-dependent diabetes mellitus (IDDM).

BACKGROUND OF THE INVENTION

Type I diabetes, or IDDM, is an autoimmune disease caused by T cells that attack and destroy the insulin-producing β-cells located in the islets of the pancreas (Castano and Eisenbarth, 1990). The autoimmune process culminating in IDDM begins and progresses without symptoms. The disease surfaces clinically only when the cumulative loss of β-cells exceeds the capacity of the residual β-cells to supply insulin. Indeed, the collapse of glucose homeostasis and clinical IDDM is thought to occur only after 80–90% of the β-cells have been inactivated by the immune system. Thus, patients who can be identified as suffering from IDDM are bound to be in an advanced stage of autoimmune destruction of their β-cells. Moreover, diagnosis of incipient, pre-clinical diabetes by the detection of immunological markers of β-cell autoimmunity can be made only after the onset of the autoimmune process. Therefore, the therapeutic quest is to find a safe, specific and effective way to turn off an autoimmune process that is already well underway.

The present inventors have examined this question before by studying the spontaneous diabetes developing in mice of the NOD strain, which is considered to be a faithful model of human IDDM (Castano and Eisenbarth, 1990). NOD mice develop insulitis around 4 weeks of age, which begins as a mild peri-islet infiltrate and progresses to severe intra-islet inflammation. Hyperglycemia, which attests to insulin insufficiency, begins in the females in our colony at about 14–17 weeks of age. By 35–40 weeks of age, almost all the female NOD mice have developed severe diabetes and most die in the absence of insulin treatment. Male NOD mice have a lower incidence of disease, for reasons that are not clear. The diabetes of NOD mice has been shown to be caused by autoimmune T cells (Bendelac et al., 1987).

T cell reactivity and autoantibodies to various antigens have been detected in human IDDM patients as well as in NOD mice (Elias, 1994), and it is not clear whether immunity to any single one of the possible target antigens is the primary cause of the disease. Beyond the question of causation is the question of therapy.

It has been demonstrated that the initiation of the autoimmune process in NOD mice can be prevented by subjecting the mice, before the onset of diabetes, to various manipulations such as restricted diet, viral infections, or non-specific stimulation of the immune system (Bowman et al., 1994). NOD diabetes is also preventable by induction of immunological tolerance in pre-diabetic mice to the antigen glutamic acid decarboxylase (Kaufman et al., 1993; Tisch et al., 1993).

Insulin dependent diabetes mellitus (IDDM) developing spontaneously in NOD female mice has been associated with immune reactivity to a variety of self-antigens (Bach, 1994). Notable among these antigens is the p277 peptide from the sequence of the mammalian 60 kDa heat shock protein (hsp60) molecule. This corresponds to residues 437–460 in the human hsp60 molecule (Elias et al 1991, Israel Patent Application No. 94241, PCT patent publication WO90/10449). The human p277 peptide has the following sequence:

Val-Leu-Gly-Gly-Gly-Cys-Ala-Leu-Leu-Arg-Cys-Ile-Pro-Ala-Leu-Asp-Ser-Leu-Thr-Pro-Ala-Asn-Glu-Asp (a.a. 437–460 of SEQ ID NO:1).

Pre-diabetic NOD mice manifest spontaneous, diabetogenic T cell responses to hsp60 and to the human (2) or mouse variants of the p277 peptide (3). The mouse and human peptides differ by 1 amino acid and are immunologicaly cross-reactive (3). Some non-diabetes prone strains of mice, such as C57BL/6, develop transient hyperglycemia and insulitis when immunized to p277 covalently conjugated to a foreign immunogenic carrier molecule (4). And mice of the C57BL/KsJ strain develop spontaneous T-cell responses to hsp60 and to p277 after treatment with a very low dose of the β-cell toxin streptozotocin (STZ) that induces autoimmune diabetes (5).

In addition to being involved in the expression of the disease, peptide p277 appears to be functional in healing the autoimmune process: Subcutaneous administration of p277 in incomplete Freund adjuvant (IFA; mineral oil) led to arrest of disease progression in young NOD mice (2) or in 12–17 week old NOD mice with advanced insulitis (6, 7). Both the human (6, 7) and mouse (3) variants of p277 were effective. NOD mice transgenic for the mouse hsp60 gene on an MHC class II promoter showed down-regulation of their spontaneous T-cell proliferative response to p277 and a significant proportion of the mice were spared the development of diabetes (8). Moreover, administration of p277 to C57BL/KsJ mice aborted the development of autoimmune diabetes in mice that had received earlier a very low dose of STZ; treatment of these mice with a peptide of the GAD65 molecule was not effective (9).

Variants of the p277 peptide in which one or both cysteine residues at positions 6 and 11 were replaced by valine residues, designated as p277(Val$^6$), p277(Val$^{11}$) and p277 (Val$^6$–Val$^{11}$), respectively, were described in corresponding Israel Patent Application No. 112094, and shown to be as active as p277 in the treatment of diabetes.

It is an object of the present invention to provide additional peptides of human hsp60, such peptides being useful for diagnosis and treatment of IDDM.

SUMMARY OF THE INVENTION

In a study of fragments and peptides of the human hsp60 molecule, it was unexpectedly found that IDDM patients and NOD mice are responsive to other hsp60 T-cell epitopes that may be used for diagnosis and therapy of IDDM. These epitopes, by themselves or in conjunction with p277 or a p277 variant selected from p277(Val$^6$), p277(Val$^{11}$) and p277(Val$^6$-Val$^{11}$), may improve the efficacy of the treatment.

These new peptides are identified in Table 1.

TABLE 1

Hsp60 Synthetic Peptides and Their Sequence

| Peptides | Residue nos. of SEQ ID NO:1 | Amino acid sequence (one letter code) |
|---|---|---|
| p3 | 31–50 | KFGADARALMLQGVDLLADA |
| p10 | 136–155 | NPVEIRRGVMLAVDAVIAEL |
| p11 | 151–170 | VIAELKKQSKPVTTPEEIAQ |
| p12 | 166–185 | EEIAQVATISANGDKEIGNI |
| p14 | 195–214 | RKGVITVKDGKTLNDELEII |
| p18 | 255–274 | QSIVPALEIANAHRKPLVIIA |
| p20 | 286–305 | LVLNRLKVGLQVVAVKAPGF |
| p24 | 346–365 | GEVIVTKDDAMLLKGKGDKA |
| p29 | 421–440 | VTDALNATRAAVEEGIVLGG |
| p30 | 436–455 | IVLGGGCALLRCIPALDSLT |
| p32 | 466–485 | EIIKRTLKIPAMTIAKNAGV |
| p35 | 511–530 | VNMVEKGIIDPTKVVRTALL |
| p39 | 343–366 | GKVGEVIVTKDDAM |

Other peptides of hsp60, including those designated p278 (corresponding to positions 458–474 in the human hsp60 sequence), p19 (corresponding to positions 271–290 in the human hsp60 sequence), and p21 (corresponding to positions 301–320 in the human hsp60 sequence)were shown not to be as effective. It is noted that the amino terminus of p278 overlaps with the effective p277 peptide by three residues (NED) and the carboxy terminus of p278 overlaps with the effective p32 peptide by 9 residues (EIIKRTLKI). Thus, the remaining 11 residues of p32 are critical (PAMTIAKNAGV).

The present invention thus relates to the peptides identified in Table 1, and salts and functional derivatives thereof.

It is further an object of the present invention to provide methods and kits for the early diagnosis of IDDM using the peptides of the invention. In the course of developing IDDM, animals express hsp60 molecules, or molecules which are cross-reactive therewith, which find their way into the blood and urine of the animals. They also express antibodies and T cells directed specifically to such molecules. Thus, the presence of hsp60 (or molecules which are cross-reactive therewith) or antibodies or T cells specific thereto in blood or urine, serves as an assay for the detection of the IDDM process before the destruction of beta cells is completed and the individual is doomed to life-long diabetes.

The presence or incipience of IDDM in a patient can be diagnosed by testing the blood or urine of said patient for the presence of antibodies or T cells which are immunologically reactive with human hsp60, using as antigen a peptide p12 or p32 of the invention.

Accordingly, the present invention provides a method for diagnosing the presence or incipience of IDDM in a patient, comprising testing said patient for the presence of anti-hsp60 antibodies or of a T cell which immunoreacts with hsp60 using a peptide of the present invention as antigen, whereby a result indicating the positive presence of anti-hsp60 antibodies or of a T cell which immunoreacts with hsp60, indicates a high probability of the presence or incipience of IDDM.

In the method for diagnosing IDDM, the patient may be tested for the presence of anti-hsp60 antibodies, wherein said test method may comprise a radioimmunoassay or an ELISA test.

The patient may also be tested for the presence of a T cell which immunoreacts with hsp60. In one embodiment of this aspect, the test method comprises a T cell proliferation test comprising the steps:

(i) preparing a mononuclear cell fraction containing T cells from a blood sample obtained from said patient;

(ii) adding to said mononuclear cell fraction an antigen selected from the peptide of the invention;

(iii) incubating said cell fraction in the presence of said antigen for a suitable period of time and under suitable culture conditions;

(iv) adding a labeled nucleotide to the incubated cell culture of (iii) at a suitable time before the end of said incubation period to provide for the incorporation of said labeled nucleotide into the DNA of proliferating T cells; and (v) determining the amount of proliferating T cells by analysis of the amount of labeled nucleotide incorporated into said T cells.

In step (iv) above, said labeled nucleotide is preferably 3H-thymidine. The determination of the amount of proliferating T cells is made by calculation of the stimulation index of the T cells by standard methods.

In another embodiment of this aspect of the invention, the test method comprises a T-cell cytokine response test, in which steps (i) to (iii) are as in the above T cell proliferation test, and in a fourth step (iv) the presence of cytokine, such as IFN-γ, IL-2, IL-4, IL-6, IL-10, TNFα or TGFβ, secreted by the responding lymphocytes into the medium, is detected by standard methods with commercially available kits.

In another aspect, the invention provides an in vivo method wherein an antigen selected from the peptides of the invention is injected subcutaneously into a patient and the occurrence of a detectable skin reaction (delayed type hypersensitivity; DTH) is observed.

The present invention also relates to means for performing such assays, as well as kits for performing such assays. The kits may be prepared for carrying out any of the various assays used for accomplishing the present invention. Each such kit includes all of the materials necessary to conduct a single assay or a fixed number of assays. For example, such a kit for determining the presence of anti-hsp60 antibodies may contain a solid-phase immobilized peptide of the invention and a tagged antibody capable of recognizing the non-variable region of the anti-hsp60 antibody to be detected, such as tagged anti-human Fab. The kit may also contain directions for using the kit and containers to hold the materials of the kit Any conventional tag or label may be used, such as a radioisotope, an enzyme, a chromophore or a fluorophore. A typical radioisotope is iodine-125 or sulfur-35. Typical enzymes for this purpose include horseradish peroxidase, horseradish galactosidase and alkaline phosphatase.

A kit for diagnosing the presence of IDDM by testing for the presence of anti-hsp60 antibodies, comprises:

(i) an antigen selected from the peptides of the invention; and (ii) a tagged antibody capable of recognizing the non-variable region of said anti-hsp60 antibodies to be detected.

A kit for diagnosing the presence of IDDM by testing for the presence of a T cell which immunoreacts with hsp60, will comprise:

(i) an antigen selected from the peptides of the invention;

(ii) a suitable medium for culture of lymphocytes (T cells); and (iii) either a labeled nucleotide for the T cell proliferation test, or a cytokine, e.g., interferon-gamma, assay kit, for the cytokine test.

For the in vivo test, the kit will comprise only a peptide of the invention in a suitable form for injection.

The present invention further relates to means for preventing or treating IDDM. Vaccination with an antigen peptide of the present invention can provide a specific down regulation of autoimmunity to the antigen, and effectively creates a resistance to the autoimmune process of IDDM. The same is true with respect to vaccination with T cells specific to such antigens, in attenuated or avirulent form or after having been treated to improve their antigenicity, or fragments or active fractions thereof. If the patient is shown to already be in the pre-clinical incipient stages of IDDM, injection with such-an antigen or T cell (or fraction) can create a down regulation of autoimmunity for this antigen and thus arrest the autoimmune process before significant, permanent damage is done. The peptide can also be used as a therapeutic agent to arrest the autoimmune process even after it is far advanced, as shown recently by the laboratory of the present inventors regarding the treatment of NOD mice with the peptide p277 (Elias and Cohen, 1994).

Accordingly, the present-invention provides a preparation for preventing or treating insulin-dependent diabetes mellitus (IDDM), comprising: (a) T cells which have developed specificity for a protein or peptide which is immunologically cross-reactive with a peptide of the invention, which cells have been activated by incubating in the presence of said peptide; (b) said T cells which have been irradiated or otherwise attenuated; (c) said T cells which have been subjected to pressure treatment by means of hydrostatic pressure, treatment with a chemical cross-linking agent and/or treatment with a cytoskeletal cross-linking agent; (d) fragments of or surface proteins shed from (a), (b) or (c) ; or (e) a peptide consisting essentially of the variable region of the receptor of (a) specific for said protein, or a salt, functional derivative, precursor or active fraction thereof.

In a preferred embodiment of the invention, the preparation comprises human T cells that have developed specificity by in vitro contact with said peptide of the invention.

The present invention also provides a pharmaceutical composition for the prevention or treatment of IDDM comprising a pharmaceutically acceptable carrier and, as active principle, an effective amount of a peptide of the invention, a salt or a functional derivative thereof.

The invention further relates to a method of preventing or treating IDDM which comprises administering to a patient in need thereof a pharmaceutical composition comprising a peptide of the invention, a salt or a functional derivative thereof, or a preparation comprising T cells which have developed specificity to said peptide of the invention.

BRIEF DESCRIPTION OF THE DRAWINGS

FIG. 3 is a graph showing T-cell proliferative responses of NOD mice to peptides. Groups of three NOD mice were immersed with peptides mouse p12, mouse p277, GAD-p35 and MT-p278 in IFA each at a dose of 25 μg in IFA. The draining lymph nodes were removed 10 days later and assayed for proliferative responses to the corresponding peptide at the concentrations of 5, 10, 20, and 50 μg/ml. The stimulation at the optimal concentration of 20 μg/ml is shown. The following ranges of cpm were obtained in medium controls: mouse p12, 881; mouse p277, 1243; MT-p278, 698 and GAD-p35 1430. Peptide mouse p38 is a peptide derived from mouse hsp60 (556–573), which has no sequence homology with the tested peptides and serves as a negative control of specificity. These results are representative of the three experiments performed. Each assay was done in triplicates for which the SD values are indicated by the bars. There was no cross-reactivity between the peptides (not shown).

DETAILED DESCRIPTION OF THE INVENTION

Whenever "peptide of the invention" or any of the individual designations, such as "peptide p12" or "peptide p32" is mentioned in the present specification and claims, also salts and functional derivatives thereof are contemplated, as long as the biological activity of the peptide with respect to diabetes is maintained.

"Salts" of the peptides of the invention contemplated by the invention are physiologically acceptable organic and inorganic salts.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

Each of the peptides of the invention can be used as the immunogen in pharmaceutical composition, particularly a vaccine for the alleviation and treatment of IDDM, as well as an antigen in diagnostic compositions for the diagnosis of IDDM. These pharmaceutical and diagnostic compositions, which may be prepared in a manner known in the art, also form part of the present invention.

The therapeutic composition in accordance with the present invention may be administered orally or parenterally, such as subcutaneously, intramuscularly, intravenously, intranasally or intrarectally.

The invention will now be illustrated in a non-limitative manner by the following Examples and accompanying figures.

EXAMPLES

Materials and Methods (i) Mice.

Inbred female mice of the NOD/Lt strain were supplied by the Animal Breeding Center of the Weizmann Institute of Science, Rehovot, Israel, or by the Jackson Laboratory, Bar Harbor, Me. These mice spontaneously develop autoimmune diabetes at 14 to 17 weeks of age that mimics IDDM in humans.

(ii) Antigens.

Peptides were synthesized in the Department of Organic Chemistry of the Weizmann Institute of Science using an automated multiple peptide synthesizer (Abimed model AMS 422; Langenfeld, Germany) following the company's protocols for N-α-fluorenylmethoxycarbonyl (Fmoc) synthesis. Crude products were purified by reversed phase HPLC on a semi-preparative C8-column (LICHROSORB RP-8, 7 mm, 250×10 mm, Merck, Darmstadt, Germany). Elution of peptides was achieved by linear gradients established between 0.1% trifluoroacetic acid in water and 0.1% trifluoroacetic acid in 75% acetonitrile in water (v/v). The purity of the single peptide products was ascertained by analytical reversed-phase HPLC and amino acid analysis. Peptide MT-p278 is from the sequence of Mycobacterial hsp60 (431–447). Peptide p277 is substituted at positions 6 and 11 with valine (V) in place of the cysteine (C) in the native sequence. Substitution of the two C residues by V enhances greatly the stability of the peptide without affecting its immunological activity: the V-substituted peptide is completely cross-reactive with the native peptide by T-cell and antibody assays. Whenever unspecified, the human sequence is intended. The mouse p12 and mouse p38 peptides are derived from the mouse hsp60 molecule and correspond to its 168–188, 437–460 and 556–573 sequences, respectively. Peptide GAD-p35 is from the GAD65 molecule (524–543). The amino acid sequences of all of the peptides used herein are shown in Table 2.

TABLE 2

Synthetic Peptides and Their Sequences

| Peptides | Sequence ID No: | Amino acid sequence (one letter code) |
|---|---|---|
| p3 | 1 (31–50) | KFGADARALMLQGVDLLADA |
| p10 | 1 (136–155) | NPVEIRRGVMLAVDAVIAEL |
| p11 | 1 (151–170) | VIAELKKQSKPVTTPEEIAQ |
| p12 | 1 (166–185) | EEIAQVATISANGDKEIGNI |
| p14 | 1 (195–214) | RKGVITVKDGKTLNDELEII |
| p18 | 1 (255–274) | QSIVPALEIANAHRKPLVIIA |
| p20 | 1 (286–305) | LVLNRLKVGLQVVAVKAPGF |
| p24 | 1 (346–365) | GEVIVTKDDAMLLKGKGDKA |
| p29 | 1 (421–440) | VTDALNATRAAVEEGIVLGG |
| p30 | 1 (436–455) | IVLGGGCALLRCIPALDSLT |
| p32 | 1 (466–485) | EIIKRTLKIPAMTIAKNAGV |
| p35 | 1 (511–530) | VNMVEKGIIDPTKVVRTALL |
| p39 | 1 (343–366) | GKVGEVIVTKDDAM |
| p19 | 1 (271–290) | LVIIAEDVDGEALSTLVLNR |
| p21 | 1 (301–320) | KAPGFGDNRKNQLKDMAIAT |
| p278 | 1 (458–474) | NEDQKIGIEIIKRTLKI |
| p277 (Val) | 2 | VLGGGVALLRVIPALDSLTPANED |
| mouse p12 | 3 | EEIAQVATISANGDKDIGNI |
| MT-p278 | 4 | EGDEATGANIVKVALEA |
| GAD-p35 | 5 | SRLSKVAPVIKARMMEYGTT |
| mouse p38 | 6 | PGMGAMGGMGGGMGGGMF |

(iii) T-Cell Proliferation to Peptides.

Mice. Nine week old NOD mice or mice of other strains were immunized in the hind foot pads with 0.1 ml of an emulsion containing 25 µg peptide in complete Freund's adjuvant (CFA; Difco, Detroit, Mich.) mixed with an equal volume of phosphate-buffered saline (PBS). The draining popliteal lymph nodes were removed 10 days later and suspensions of lymphocytes in triplicate cultures were tested for proliferation in the presence of the various peptides (5 µg/ml) using the incorporation of [$^3$H]-thymidine as described (Elias et al., 1991). The results are shown as the stimulation index (SI): the ratio of the mean cpm in the presence of the test peptide to the mean cpm of control cultures without the peptide. Standard errors were always less than 10% of the means.

(iv) Treatment and follow-up.

Peptides, 100 mg, in PBS, were emulsified with an equal volume of IFA and injected subcutaneously into 10-week-old NOD females as described (Elias and Cohen, 1995). Control mice received an equal volume of PBS emulsified in IFA. The mice were monitored monthly for non-fasting blood glucose at 10 am using the Blood Glucose Sensor (MediSense. Inc., Waltham, Mass.). Mice with a blood glucose greater than 11.1 mmol/L were considered to be diabetic; this concentration of glucose was greater than 3 standard deviations above the mean blood glucose concentration measured in non-diabetic mice (Elias and Cohen, 1995). Histological examination of the islets of the pancreas was done on sections stained with hematoxylin and eosin. The sections were scored independently by two observers who both were unaware of the identity of the groups. The chi square test was used to ascertain the statistical differences between the various treatments.

(v) Serum Antibodies.

Mice were bled monthly to detect antibody responses. The ELISA assay was done as described (Elias et al., 1991). Briefly, flat bottom Maxi-sorb plates (Nunc, Roskilde, Denmark) were coated, for the detection of anti-peptide antibodies, with 100 ml/well of peptide in PBS, at a concentration of 10 mg/ml for 2 h at room temperature followed by over night incubation at 4° C. After incubation with peptide, the plates were washed and blocked for 2 h at 37°

C. with 7% BSA (Sigma) in PBS. Sera were diluted 1:50 then added for 2 h at 37° C., followed by incubation for 2 h with 100 ml per well of goat anti-mouse IgG (gamma chain Fc specific) conjugated to alkaline phosphatase (Jackson, Philadelphia, Pa.). After washing, the plates were incubated with the substrate, diethanolamine (Sigma) and read using an ELISA reader at 405 nm.

Example 1
Mapping of Hsp60 Epitopes in NOD Mice

Figure 1:
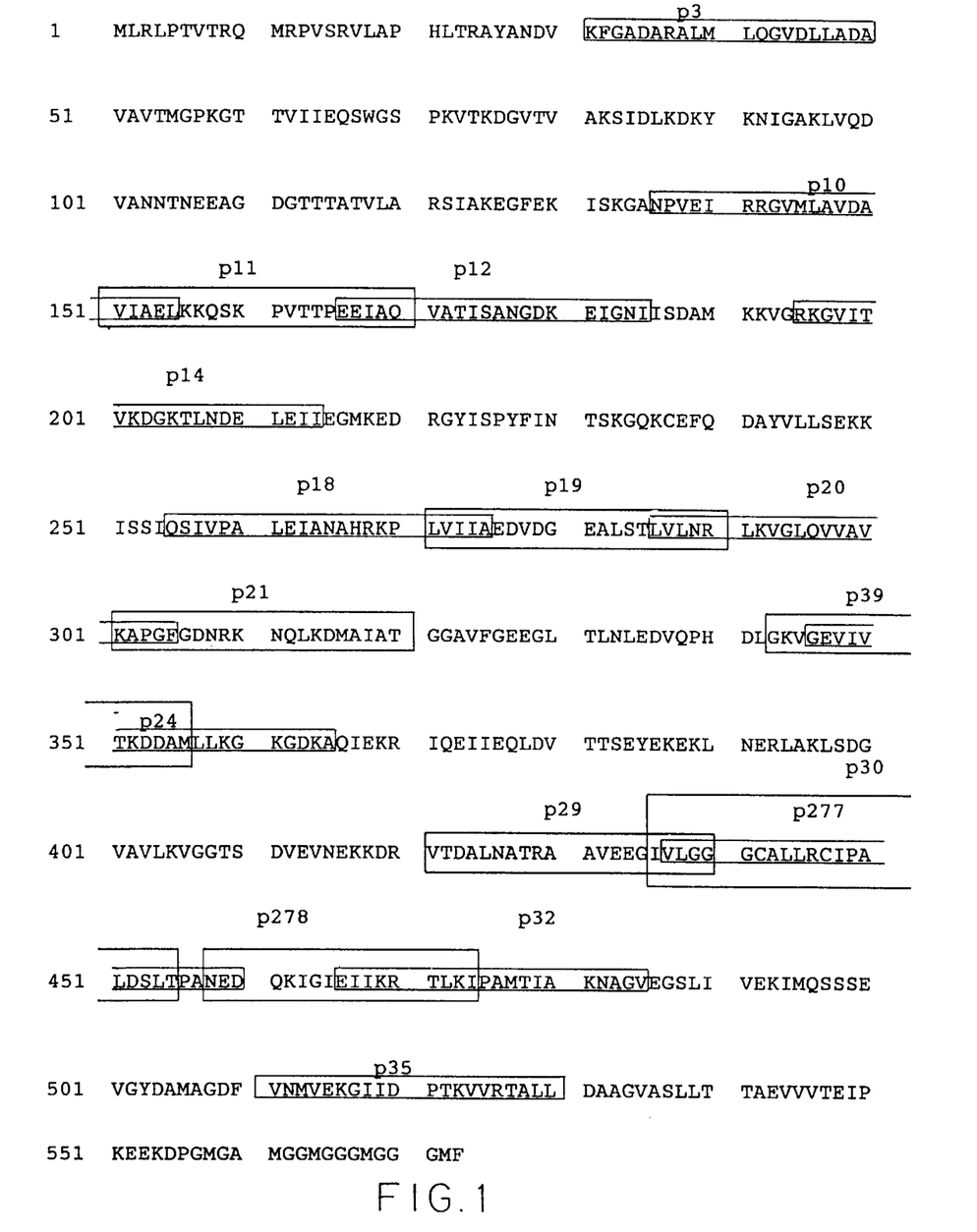
FIG. 1 shows the positions of the peptides referred to herein on the entire sequence of the human hsp60 molecule.
Figure 2:
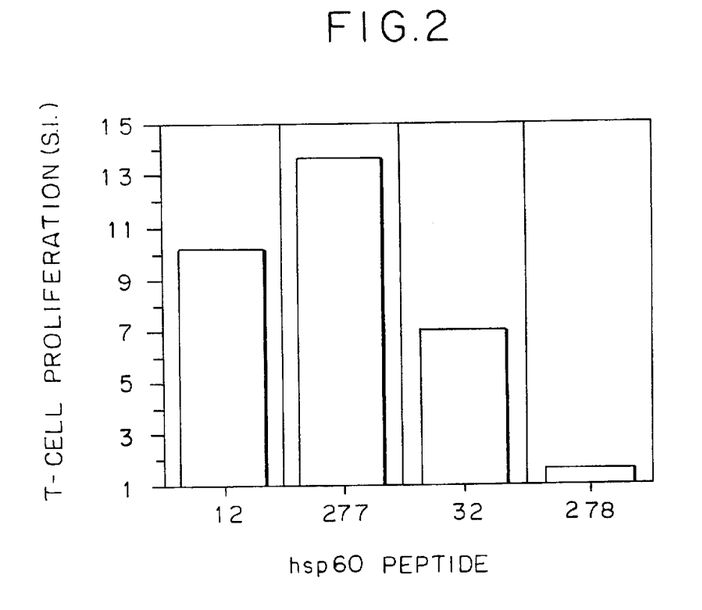
FIG. 2 shows NOD mouse T-cell proliferation to human hsp60 peptides p12, p32, p277 ($Val^6$–$Val^{11}$) and p278.

The immunogenicity of the hsp60 peptides p12, p32, p277(Val$^6$–Val$^{11}$) and p278 in NOD mice was tested by immunizing the mice with the peptides emulsified in CFA in the hind foot pads, and assaying the proliferative responses of draining lymph node cells after 10 days as described above in section iii(a). As shown in FIG. 2, the peptides p277 (Val$^6$–Val$^{11}$), p12 and p32 were strongly immunogenic, while p278 was non-immunogenic.

Example 2
Treatment of NOD Mice with p277 (Val$^6$–Val$^{11}$), p12 or p32

To test whether the p12 and p32 peptides can block the progression of diabetes as p277 (Val$^6$–Val$^{11}$), the p277 (Val6–Val$^{11}$), p12 or p32 peptides (100 μg in a 0.1 cc emulsion of IFA) were administered subcutaneously to groups of 10–12 nine-week old NOD/Lt female mice of the Jackson Laboratory, Bar-Harbor, Me. Diabetes, determined as persistent blood glucose levels over 11.1 mmol/l, was tested at 25 weeks of age. Control mice were untreated or were treated with p278.

As shown in Table 1, p277 (Val6–Val$^{11}$), p12 and p32 were effective in treatment of diabetes, the incidence of diabetes in untreated mice or in p278-treated mice being 90%, while p277 (Val$^6$–Val$^{11}$), p12 and p32-treated mice show an incidence of 10%, 20% and 30%, respectively. On the other hand, the control p278 peptide had no therapeutic effect.

TABLE 3

Therapeutic effect of hsp60 peptides

| Peptide | Diabetes (%) | Mortality (%) | Number of Recipients |
| --- | --- | --- | --- |
| none | 90 | 50 | 100 |
| p278 | 90 | 45 | 100 |
| p277(Val$^6$–Val$^{11}$) | 10* | 5* | 100 |
| p12 | 20* | 10* | 10 |
| p32 | 50* | 25* | 20 |

*P < 0.05

It is possible that a combination of two or three hsp60 epitope peptides will be more effective than only one peptide, as more T-cell populations will be affected by the therapy.

Example 3
Newly Diagnosed IDDM Patients show T-cell Proliferative Responses to hsp60, p277 (Val$^6$–Val$^{11}$), p12 and p32

To determine the T-cell responses to the various hsp60 peptides, lymphocytes from the peripheral blood of newly diagnosed (2 weeks-4 months) IDDM patients were tested in a proliferation assay. 10–20 ml of blood were removed into a sterile tube containing heparin as anti-coagulant and diluted in PBS 1:2. Peripheral mononuclear cells (PBMC) were isolated by centrifuging the blood over a lymphoprep layer. The PBMC were tested for proliferation in triplicates, in the presence of the various antigens (10 μg/ml) for 6 days using the incorporation of [$^3$H]-thymidine as a measure of proliferation. The antigens tested were human hsp60 or the hsp60 peptides p277 (Val$^6$–Val$^{11}$), p12, p32 and control peptide p278. The T cell proliferative response is depicted as stimulation index (SI): The ratio between peptide-stimulated thymidine incorporation and background (no antigen added) thymidine incorporation by the T cells.

TABLE 4

| Patient to: | T-cell proliferative response(SI) | | | | |
| --- | --- | --- | --- | --- | --- |
|  | hsp60 | p277(V) | p12 | p32 | p278 |
| 1 | 5.6 | 4.5 | 4.0 | 1.1 | 0.5 |
| 2 | 7.5 | 5.0 | 4.5 | 1.3 | 0.8 |
| 3 | 8.0 | 5.6 | 1.2 | 7.1 | 0.7 |
| 4 | 3.4 | 1.0 | 1.9 | 2.9 | 0.9 |
| 5 | 1.2 | 1.1 | 1.7 | 1.0 | N.D. |
| 6 | 6.7 | 1.3 | 5.2 | 4.5 | N.D. |
| 7 | 10.3 | 3.9 | 1.2 | 6.0 | N.D. |
| 8 | 1.3 | 1.2 | 1.5 | 1.1 | N.D. |

A stimulation index (SI) of more than 2.0 is considered a positive response.
N.D. = Not determined; p277(V) = p277(Val$^6$–Val$^{11}$)

It can be seen that most of the patients responded to hsp60 (6/8) and that all of the six that responded to hsp60 also responded to at least one of the three hsp60 peptides: p12, p32 or p277 (Val$^6$–Val$^{11}$). Thus, a response to the group of the peptides can serve to characterize the individuals responding to the whole hsp60 molecule.

Example 4
T cell Proliferative Responses

Figure 3:
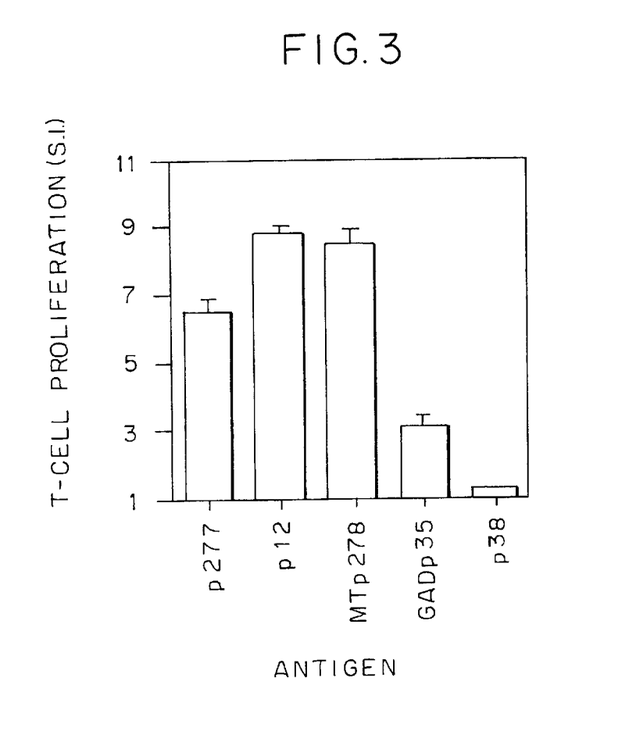

Spontaneous T cell responses in pre-diabetic NOD mice were detected to the mouse p277 peptide (Elias et al., 1991; Birk et al., 1996) and to larger fragments of the mouse hsp60 molecule that contained the mouse p277 sequence (Birk et al., 1996). To detect other T-cell epitopes on the mouse hsp60 molecule, NOD mice were immersed with pools of peptides overlapping the hsp60 sequence and found that all mice made strong response to both mouse p277 and to mouse p12 (FIG. 3). Other peptides immunogenic for NOD mice are the MT-p278 peptide (residues 458–474 in the Mycobacterial hsp60 molecule), and GAD-p35 (residues 524–543 in the GAD65 molecule). FIG. 3 shows that MT-p278 is as strongly immunogenic as are mouse p277 and mouse p12; GAD-p35 is also immunogenic, but less so.

A longitudinal study of female NOD mice at ages 3–16 weeks showed no spontaneous responses to mouse p12 in their spleens (not shown), although responses to mouse p277 and to whole mouse hsp60 were seen. Thus, of four immunogenic peptides: p12 and p277 from the mouse hsp60 molecule, GAD-p35 from the diabetes-associated GAD65 molecule, and MT-p278, a foreign immunogen, spontaneous responses were detected only to mouse p277 and to MT-p278.

Peptide Treatment

Figure 4:
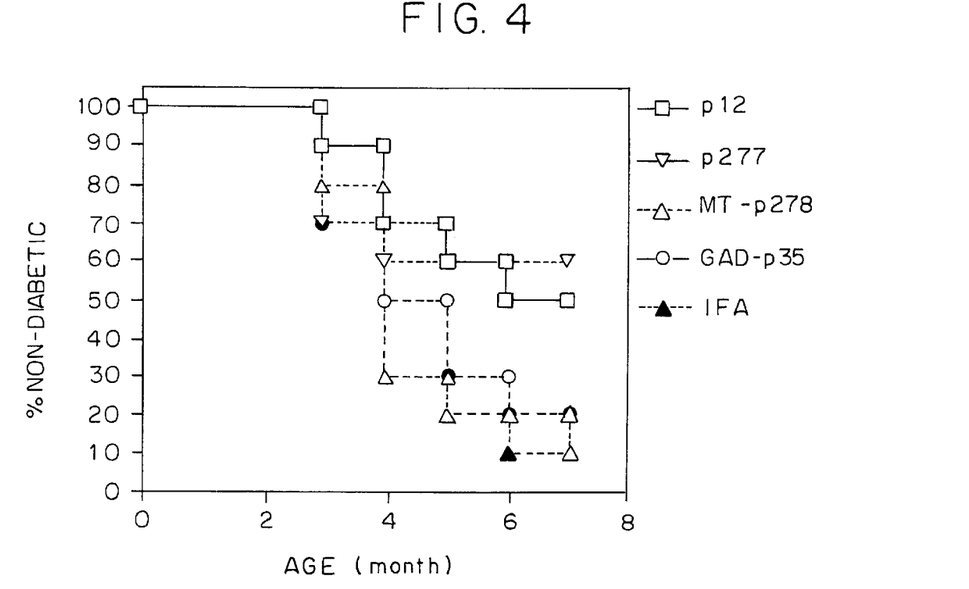
FIG. 4 is a graph showing the effect of peptide administration on diabetes. Groups of 10–20 NOD mice were treated at 10 weeks of age with 100 μg of mouse p12, p277, p35-GAD or MT-p278 in IFA, or IFA alone. The mice were bled monthly and followed for the onset of hyperglycemia. As compared to the IFA treated control group, the mice treated with p12 and p277 were significantly protected, $P<0.05$.
Figure 5A:
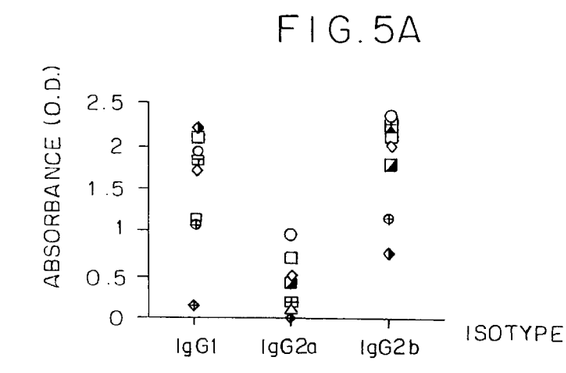
FIG. 5A–5D show the IgG1, IgG2a and IgG2b antibody isotypes in response to peptide treatment. Mice were treated as described in the legend to FIG. 4. Individual samples were analyzed for antibodies to mouse p12 A; p277 B; GAD-p35 C; and MT-p278 D, of the IgG1, IgG2a and IgG2b isotypes. Similar effects were obtained in two experiments. The results are presented as the absorbance at 405 nm (OD) of 10 individual mice in each group. The level of significance of the prevalence of IgG1 and IgG2b antibodies in groups A and B compared to C and D is $P<0.001$. The differences between the levels of IgG1 and IgG2b antibodies compared to the IgG2a antibodies in groups A and B were significant ($P<0.001$). There was no cross-reactivity between the antibodies (not shown).
Figure 5B:
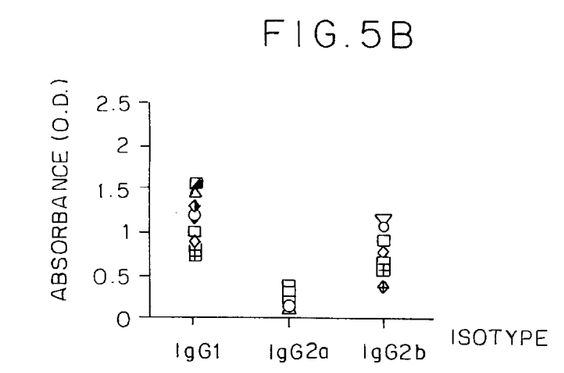
Figure 5C:
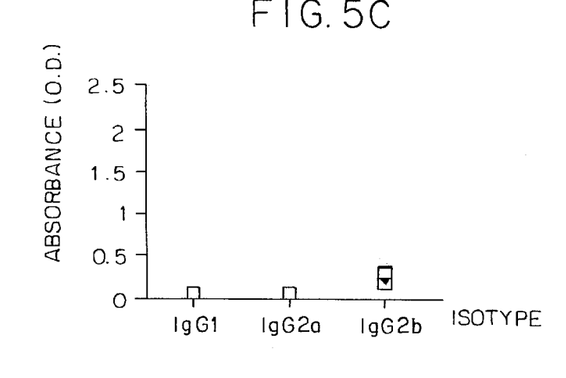
Figure 5D:
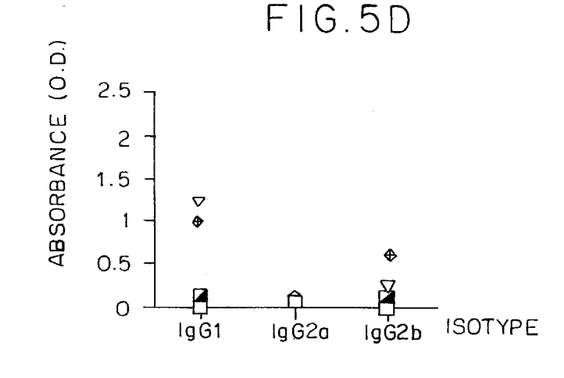

Following a protocol shown to be effective with mouse p277 (Elias et al., 1991; Elias and Cohen, 1994; Elias and Cohen, 1995), groups of 10-week old female NOD mice were treated by a single subcutaneous injection of each peptide (100 mg) emulsified in IFA. The mice were observed for the development of diabetes through 8 months of age. FIG. 4 shows that peptides mouse p277 and mouse p12 were both effective in inhibiting the development of diabetes (P<0.05). In contrast, treatment with peptides MT-p278 or GAD-p35 was no different than was treatment with IFA alone. A total of 3 experiments showed essentially the same results.

Antibodies

Successful treatment of STZ-induced diabetes with mouse peptide p277 was associated with the appearance of anti-peptide antibodies predominantly of the IgG1 and IgG2b isotypes (Elias and Cohen, 1996). The peptide-treated NOD mice for their serum antibodies was therefore examined. FIGS. 5A–5D show that the two peptides effective in arresting diabetes, mouse p12 and mouse p277, were also effective in inducing strong antibody titers of the IgG1 and IgG2b isotypes (P<0.001). The IgG1 and IgG2b antibody titers were also significantly greater than the IgG2a antibody titers in these groups (p<0.001). The mice treated with peptides MT-p278 or GAD-p35 did not respond as strongly; none of the GAD-p35-treated mice made specific IgG1 antibodies and only two of the ten MT-p278-treated mice made antibodies of the IgG1 isotype. The mice treated with MT-p278 or GAD-p35 made significantly lower titers of IgG2b antibodies (P<0.001). Thus, effectiveness in inhibiting diabetes was associated with the induction of an antibody response mainly of the IgG1 and IgG2b isotypes.

Figure 6:
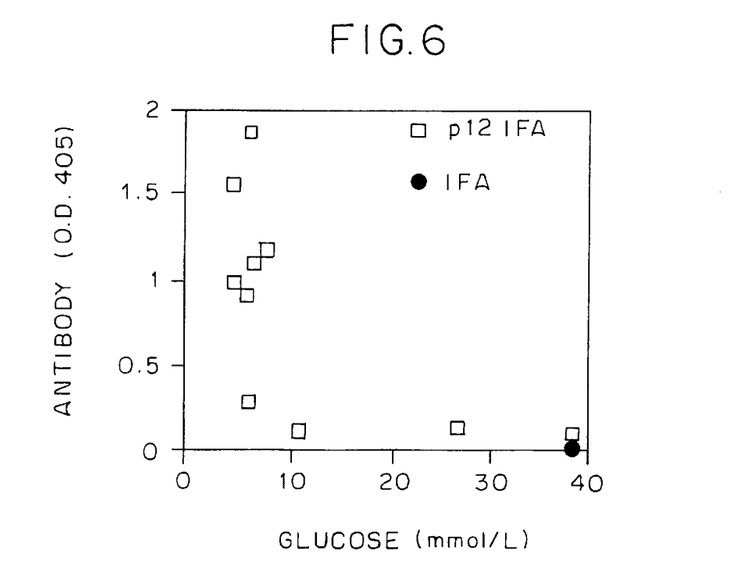
FIG. 6 shows the negative correlation between antibodies and blood glucose. A group of NOD female mice were treated with p12 (10 mice) or with IFA alone (9 mice) as described in the legend t FIG. 4. The amount of anti-p12 specific antibody (ELISA O.D units in sera diluted 1:50, measured at 7 months of age) is plotted together with the blood glucose concentration measure at 7 months of age. The degree of correlation between high antibodies and blood glucose is $P<0.002$.

The relationship between an effective therapeutic response and the titer of antibody was confirmed by a comparison of the concentration of the blood glucose with the concentration of antibodies in individual mice at 7 months of age. FIG. 6 shows that the mice with higher titers of anti-mouse p12 antibodies tended to have lower blood glucose concentrations; conversely, the mouse p12-treated mice that made little antibody to mouse p12 tended to have high blood glucose (P<0.002).

DISCUSSION

The results presented in this example indicate that peptide p12 of the mouse hsp60 molecule, like peptide p277, can be effective in treating mice close to the outbreak of overt hyperglycemia. In contrast to p277, spontaneous T-cell proliferative responses to p12 in the spleens of pre-diabetic NOD mice were not observed. Thus, a spontaneous anti-peptide proliferative response detectable in the periphery is not a requirement for a peptide to be effective in blocking the diabetic autoimmune process.

The finding that peptide p277 is not the only hsp60 peptide that can modulate NOD diabetes is significant. It was conceivable that the involvement of hsp60 in NOD diabetes could have come about by mimicry between the p277 peptide of hsp60 and some unknown molecule more specific for β-cells (Cohen, 1991). However it is highly unlikely that two different segments of hsp60, p277 and p12, could both mimic segments of the proposed, but unknown β-cell molecule. The effectiveness of p12 in peptide treatment supports the conclusion that the hsp60-like molecule functional in diabetes is hsp60 itself (Birk et al., 1996).

The failure of peptide MT-p278 and GAD-p35 to arrest the development of diabetes indicates that not any self-antigen or any spontaneously T-cell proliferating antigen can be used to abort the autoimmune process. It is interesting, that MT-p278 failed to induce high titers of antibodies or protect, despite the fact that their peptide is strongly immunogenic for T cells (unpublished observation). However, the induction of antibodies of any specificity does not necessarily affect NOD diabetes; treatment of NOD mice with BSA, which induces high titers of antibodies as well as strong T cell responses (not shown), does not affect the development of diabetes (Elias and Cohen, 1994). Although GAD-p35 was not found by us to be as strongly immunogenic for T cells as were the other peptides (FIG. 3). NOD mice have been reported to manifest spontaneous T cell responses to their peptide (Kaufman et al., 1989).

Finally, the association of effective treatment with induction of antibody specific to the peptide suggests that the therapeutic effects of p12 and p277 might be related to the activation of Th2-type T cells responsible for helping the induction of specific IgG1 antibodies, antibodies regulated by the production of IL-4 (Mossman and Coffman, 1993). Such T cells could suppress the Th1 T cells thought to be proposed to be responsible for damaging the β-cells (Katz et al., 1995; Liblau et al., 1995). Indeed, it has been found that p277 peptide therapy of NOD diabetes is associated with a burst of IL-4 and IL-10 producing T cells in the spleen and a fall in the T cells producing INF-γ both in the spleen and in the islets (unpublished observation). The appearance of peptide-specific antibodies bearing Th2 isotypes in response to peptide therapy appears to be an indicator of a beneficial response.

Example 5—Additional Peptides to Which IDDM Patients can Manifest T-cell Responses Twenty six newly diagnosed (1 to 16 weeks after IDDM diagnosis) IDDM patients were enrolled. Patients' ages ranged from 5 to 60 years old. The patients were screened for their peripheral blood T-cell proliferative responses to human hsp60, and to human hsp60 synthetic peptides shown in Tables 1 and 5, which are portions of the human hsp60 protein sequence.

The patients' T-cells were analyzed also for their proliferative responses to standard recall antigens such as tetanus toxoid, Candida albicans and influenza, and the responses were scored as positive if the stimulation index (S.I.) was 2 or greater (see below).

Proliferation was assayed using the following protocol:
Cell Preparation and Cell Proliferation Protocol Fifty ml of peripheral blood supplemented with 10 IU/ml heparin was drawn from IDDM patients or from healthy controls. Two volumes of PBS (calcium- and magnesium-free) were added. The blood-PBS preparation was mixed using a 10 ml pipette. A volume of 10 ml Ficoll was underlaid in the blood mixture, followed by centrifugation at 2,000 rpm for 30 minutes at room temperature (R.T.) 20–24° C. (brake off). The peripheral blood T-cells in the buffy coat were harvested using a 10 ml pipette and transferred to a new 50 ml test tube. A volume of 30 to 40 ml PBS (calcium- and magnesium-free) was added to the harvested T-cells. This was then mixed and centrifuged at 1,000 rpm for 20 minutes at R.T. (brake on).

The supernatant was aspirated, and the pellet of cells was resuspended in AIM-V serum free culturing media (GIBCO, USA). The culture medium contains AIM-V supplemented with 1% sodium-pyruvate, 1% L-glutamine (200 mM each), 1% penicillin/streptomycin (10,000 U/ml/10,000 mg/ml and 2% Hepes (1 M, pH 7.3). Alternatively, RPMI supplemented with 10% AB serum from the blood bank was used. The cell mixture was then centrifuged at 2,000 rpm for 10 minutes at R.T. (brake on). The suernatant was again aspirated and the pellet of cells resuspended in a smaller volume of fresh AIM-V (10–20 ml). The cells were resuspended and counted. Cell counting and viability assays were performed using trypan blue. For this step a hemocytometer and a light microscope were used.

The cell concentration was then adjusted to $2 \times 10^6$ cells/ml in AIM-V media. A volume of 100 μl of the cells per well were transferred to each well of a 96-well microtiter plate. Then, 100 μl of media containing two-fold the recommended antigen concentration (see below list of antigens and concentrations) was added. The assay was performed in quadruplicate. Four wells were assayed with cells and media without antigen as a control. The plates were cultured at 37 C° in a 5% $CO_2$ humidified incubator for 7 days. On day 6 of the culturing period, 1 μCi/well of $^3$H-thymidine was added. The cultures were continued for 18 hours and then harvested. Cell proliferation was assayed by $^3$H-thymidine incorporation to DNA, determined using scintillation liquid and a beta counter reader.

| Antigens Tested | Concentration |
| --- | --- |
| Tetanus toxoid (Connaught Lab. Inc. Pen. USA) | 5 g/ml |
| Candida albicans (Miles, WA. USA) | 20 μg/ml |
| Recombinant human hsp60 (StressGen, Canada) | 2–5 μg/ml |
| Human hsp60 synthetic peptides | 20 μg/ml |

Proliferative responses were measured according to the thymidine $^3$H incorporated by T cells' DNA (Elias et al., 1991). Radioactive counts per minute (CPM) were compared between cells cultured with the tested antigens or without antigen (media only) as a control. The proliferation values were represented as a stimulation index value (S.I.): mean CPM with the antigen divided by the mean CPM without the antigen. S.I. values greater than or equal to 2 were considered to be positive.

The results showed that the incidence of human hsp60 or hsp60-peptide reactive individuals was higher among IDDM patients (84%) than among healthy people (30%). The Fisher Exact Test p value of the difference is 0.0044, which is highly significant.

Figure 7:
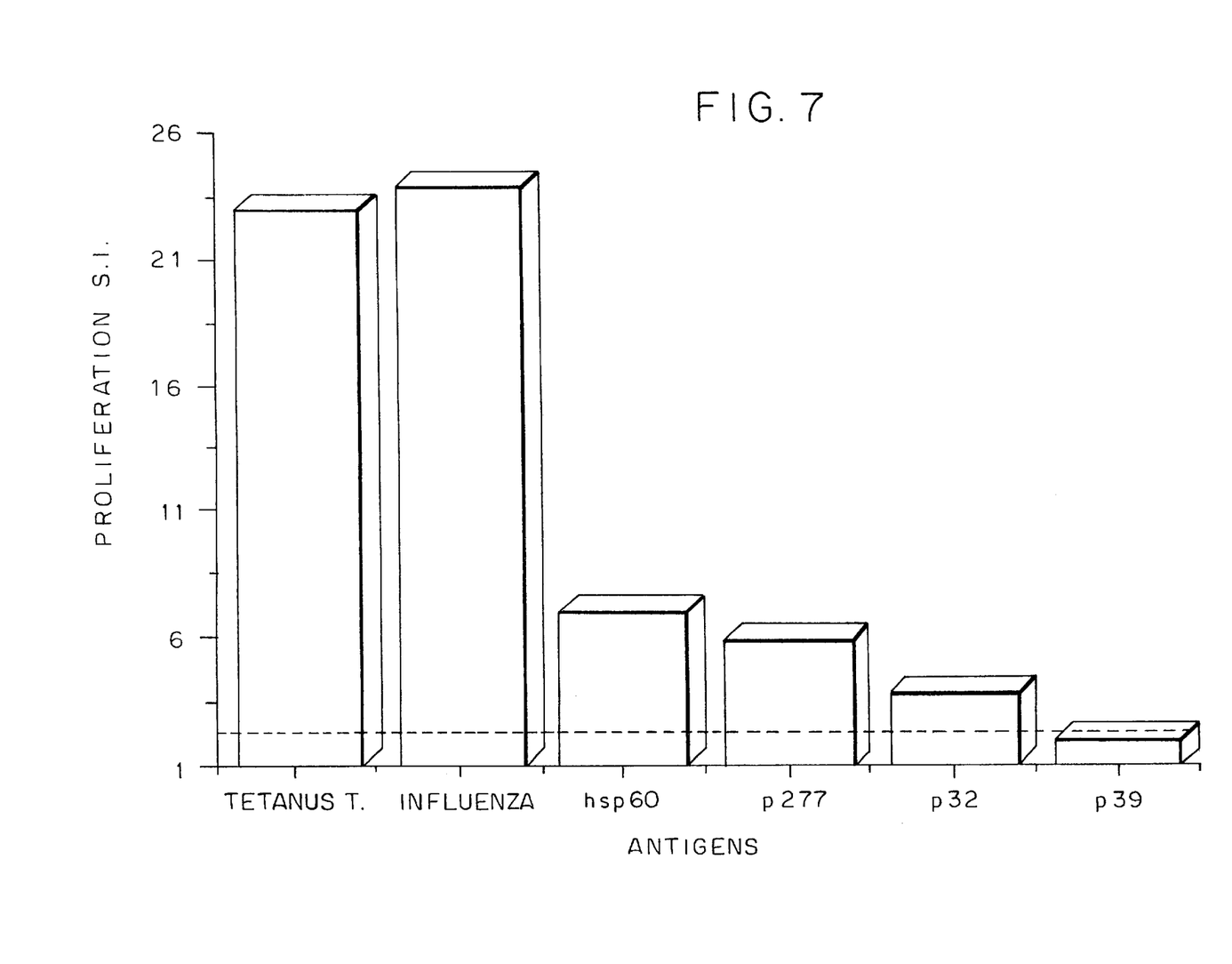
FIG. 7 is a graph showing T-cell proliferative responses (S.I.) of one IDDM patient donor to recall antigens, to hsp60 protein, and to hsp60 synthetic peptides.
Figure 8:
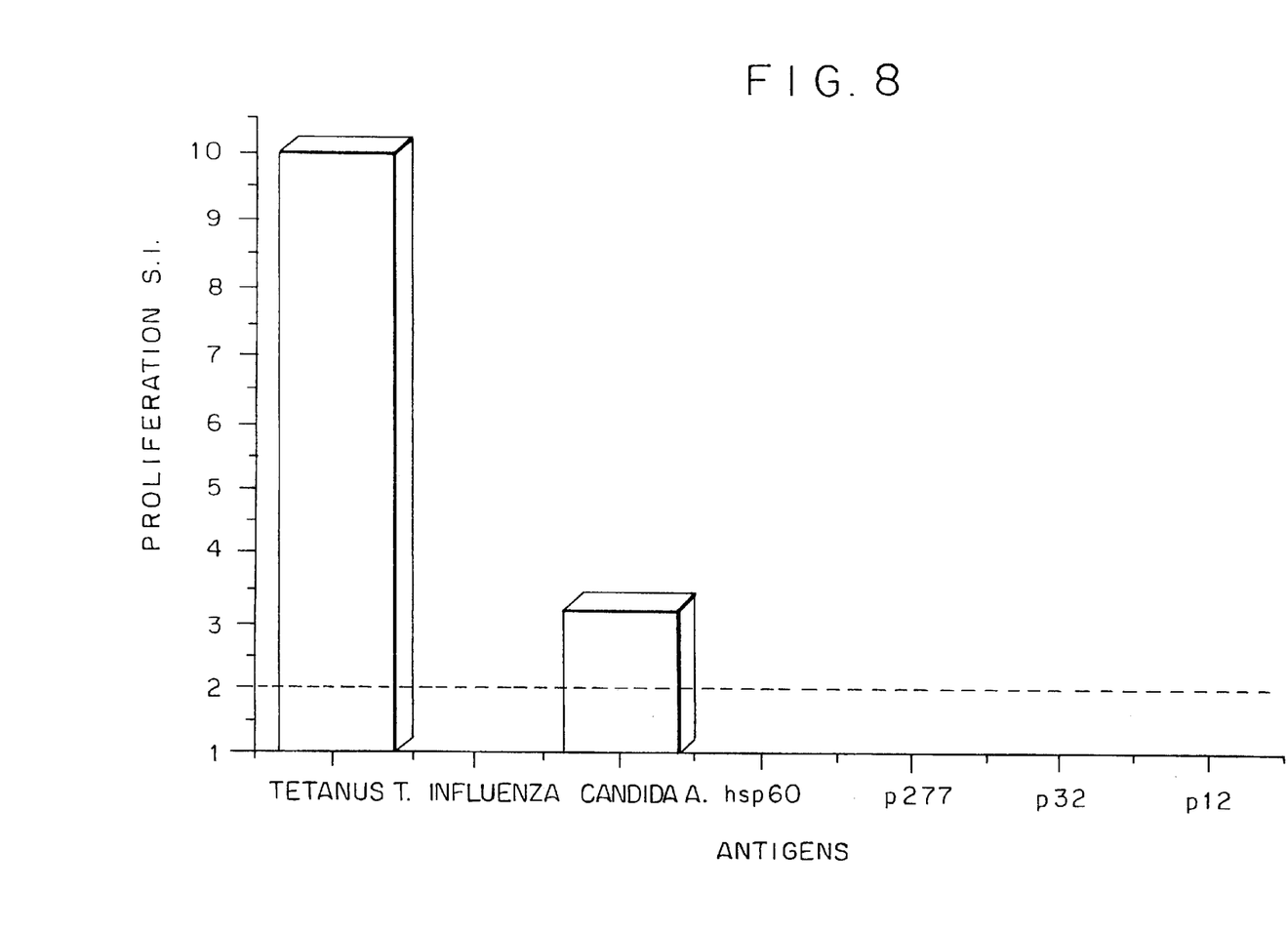
FIG. 8 is a graph showing T-cell proliferative responses (S.I.) of a healthy donor to recall antigens, to hsp60, and to hsp60 synthetic peptides.
Figure 9:
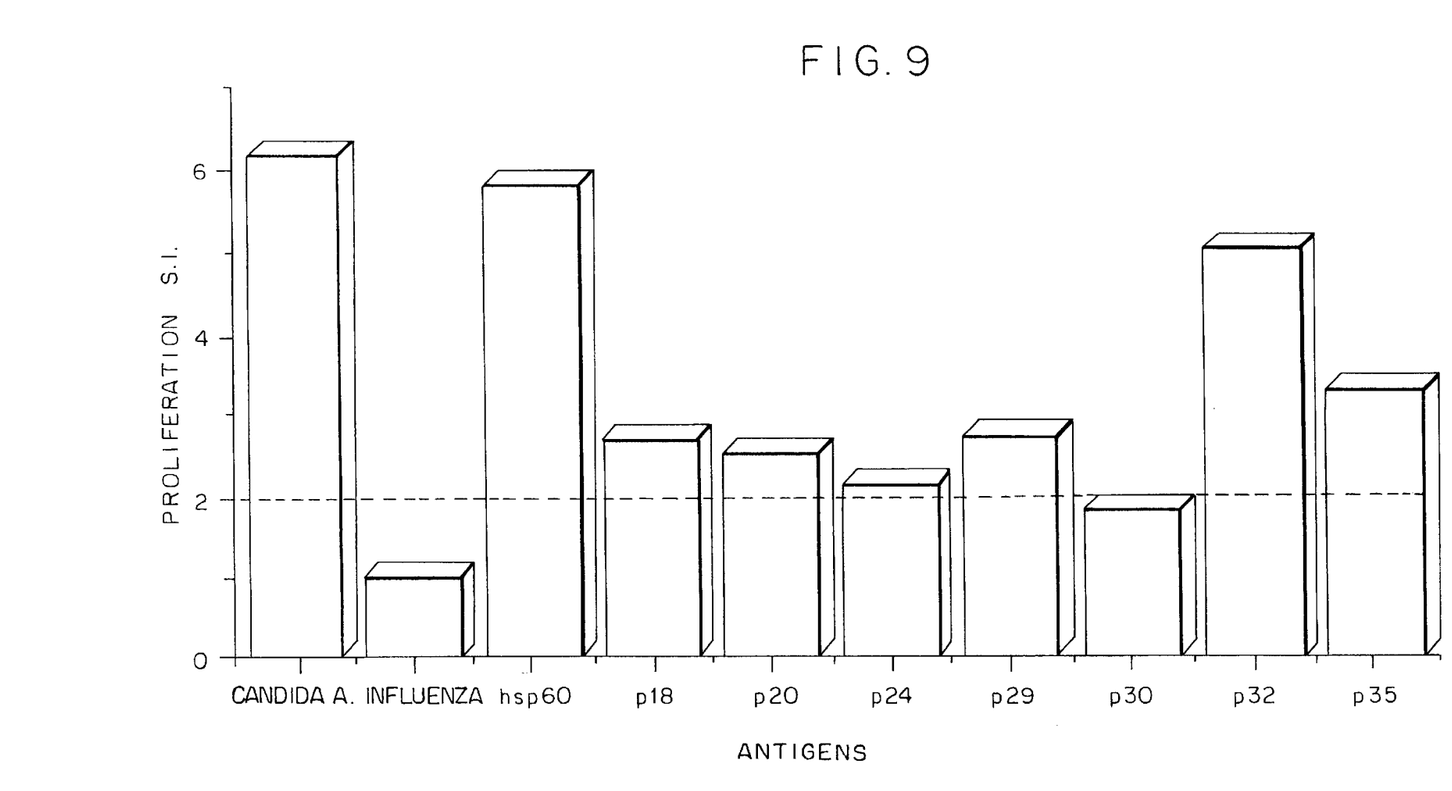
FIG. 9 is a graph showing T-cell prolifereative responses (S.I.) of another IDDM patient donor to recall antigen, to hsp60 and to hsp60 synthetic peptides.
Figure 10A:
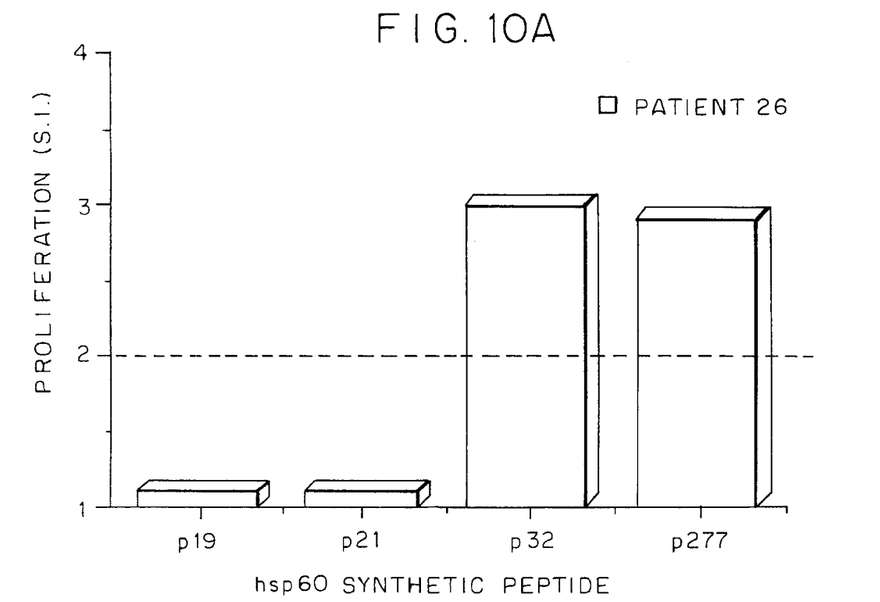
FIGS. 10A and 10B are graphs showing T-cell proliferative responses (S.I.) of two IDDM patient donors to hsp60 synthetic peptides.
Figure 10B:
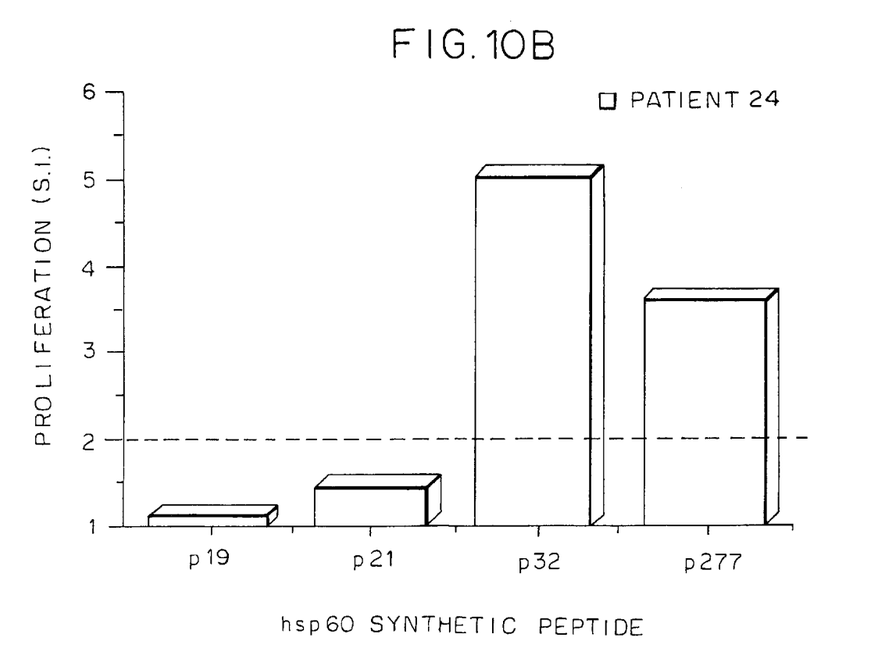

Proliferative responses of two representative IDDM patients and of one healthy individual, to human hsp60 protein, to hsp60 synthetic peptides, and to various recall antigens are shown in FIG. 7, 8, and 9. Table 5 shows two individual examples of hsp60 synthetic peptides (p19, p21) to which no IDDM patients responded (see also FIGS. 10A and 10B).

It can be seen that each of the patients responded to recall antigens (Candida, tetanus, or influenza) and to human hsp60 protein and to various human hsp60 peptides. The control person responded only to control recall antigens.

The sequences of the hsp60 synthetic peptides to which at least one of the IDDM patients responded are shown in Table 1. Each of these peptides has therapeutic potential for treating IDDM.

TABLE 5

Hsp60 Synthetic Peptides and Their Sequence to Which IDDM Patients

Did Not Respond

| Peptides | Residue nos. of SEQ ID NO:1 | Amino acid sequence (one letter code) |
| --- | --- | --- |
| p19 | 271–290 | LVIIAEDVDGEALSTLVLNR |
| p21 | 301–320 | KAPGFGDNRKNQLKDMAIAT |

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Bach J. F. (1994) Insulin-Dependent Diabetes Mellitus as an Autoimmune Disease. *Endocrine Reviews* 15:516–542.

Bendelac A, Carnaud C, Boitard C, Bach J. F. (1987) Syngeneic transfer of autoimmune diabetes from diabetic NOD ice to healthy neonates. Requirement for both L3T4+ and Ly+–2+ T cells. *J Exp Med.* 166: 823–32.

Birk O. S., Elias D, Weiss A. S., Rosen A, van-der Zee R, Walker M. D., Cohen I. R. (1996) NOD mouse diabetes: The ubiquitous mouse hsp60 is a beta-cell target antigen of autoimmune T cells. *J. Autoimmun.* 9:159–166.

Bowman M. A., Leiter E. H. and Atkinson M. A. (1994) Prevention of diabetes in the NOD mouse: implications for therapeutic intervention in human disease. *Immunology Today.* 15:115–20.

Castano L, Eisenbarth G. S. (1990) Type-I diabetes: a chronic autoimmune disease of human, mouse, and rat. *Annu Rev Immunol.* 8:647–79.

Cohen I. R. (1991) Autoimmunity to chaperonins in the pathogenesis of arthritis and diabetes. *Annu Rev Immunol* 9:567–589.

Elias, Dana. (1994) The NOD mouse: A model for autoimmune insulin-dependent diabetes. *Autoimmune Disease Models, A Guidebook*, pp 147–61.

Elias D, Cohen I. R. (1995) Treatment of autoimmune diabetes and insulitis in NOD mice with heat shock protein 60 peptide p277. *Diabetes* 44:1132–1138.

Elias D, Reshef T, Birk O. S., van der Zee R, Walker M. D., Cohen I. R. (1991) Vaccination against autoimmune mouse diabetes with a T-cell epitope of the human 65 kDa heat shock protein. *Proc. Natl Acad Sci USA.* 88:3088–91.

Elias D. and Cohen I. R. (1994) Peptide therapy for diabetes in NOd mice. *The Lancet.* 343:704–706.

Elias D, Cohen I. R. (1996) The hsp60 peptide p277 arrests the autoimmune diabetes induced by the toxin streptozocin. *Diabetes* (in press).

Katz J. D., Benoist C, Mathis D. (1995) T helper cell subsets in insulin-dependent diabetes. *Science* 268:1185–1188.

Kaufman D. L., Clare-Salzler M, Tian J, Forsthuber T, Ting GSP, Robinson P, Atkinson M. A., Sercarz E. E., Tobin A. J., Lehmann P. V. (1993) Spontaneous loss of T-cell tolerance to glutamic acid decarboxylase in murine insulin-dependent diabetes. *Nature.* 366:69–72.

Liblau R. S., Singer S. M., McDevitt H. O. (1995) Th1 and Th2 CD4+ T cells in the pathogenesis of organ-specific autoimmune diseases. *Immunol Today* 16:34–38.

Mossman TRR, Coffman R. L. (1989) TH1 and TH2 cells: Different patterns of lymphokine secretion lead to different functional properties. *Annu Rev Immunol* 9:145–173.

Tisch R, Yang X. D., Singer S. M., Liblav R. S., Fuggar L, McDevitt H. O. (1993) Immune response to glutamic acid decarboxylase correlates with insulitis in non-obese diabetic mice. *Nature.* 366:72–75.

What is claimed is:

1. A peptide selected from the group consisting of the peptides consisting of residue nos. 31–50, 136–155, 151–170, 166–185, 195–214, 255–274, 286–305, 346–365, 421–440, 436–455, 466–485, 511–530 and 343–366 of SEQ ID NO:1, and salts and functional derivatives thereof wherein said functional derivatives consist of chemical modifications to amino acid side chains and/or the carboxyl and/or amino moieties of said peptides.

2. A pharmaceutical composition comprising a peptide according to claim 1 and a pharmaceutically acceptable carrier.

3. A pharmaceutical composition according to claim 2 for the prevention or treatment of IDDM.

4. A peptide in accordance with claim 1 selected from the group consisting of the peptides consisting of residue nos. 31–50, 136–155, 151–170, 166–185, 195–214, 255–274, 286–305, 346–365, 421–440, 466–485, 511–530 and 343–366 of SEQ ID NO:1, and salts and functional derivatives thereof, wherein said functional derivatives consist of chemical modifications to amino acid side chains and/or the carboxyl and/or amino moieties of said peptides.

5. A peptide in accordance with claim 1 selected from the group consisting of the peptides consisting of residue nos. 31–50, 136–155, 151–170, 166–185, 195–214, 255–274, 286–305, 346–365, 421–440, 436–455, 466–485, 511–530 and 343–366 of SEQ ID NO:1 and salts thereof.

6. A peptide in accordance with claim 1, wherein said peptide is that of residues 166–185 of SEQ ID NO:1 or a salt or functional derivative thereof, wherein said functional derivative consists of chemical modifications to amino acid side chains and/or the carboxyl and/or amino moieties of said peptides.

7. A pharmaceutical composition comprising a peptide according to claim 6 and a pharmaceutically acceptable carrier.

8. A peptide in accordance with claim 1, wherein said peptide is that of residues 466–485 of SEQ ID NO:1 or a salt or functional derivative thereof, wherein said functional derivative consists of chemical modifications to amino acid side chains and/or the carboxyl and/or amino moieties of said peptides.

9. A pharmaceutical composition comprising a peptide according to claim 8 and a pharmaceutically acceptable carrier.

10. A composition comprising a peptide in accordance with claim 1 in conjunction with a peptide selected from the group consisting of p277, p277 (Val$^6$), p277 (Val$^{11}$) and p277 (Val$^6$-Val$^{11}$).

11. A method for diagnosing the presence or incipience of IDDM in a patient, comprising testing the blood or urine of said patient with a peptide according to claim 1 as antigen for the presence of antibodies or T cells which are immunologically reactive with human hsp60, whereby a result indicating the positive presence of anti-hsp60 antibodies or of a T cell which immunoreacts with hsp60 indicates an increased probability of the presence or incipience of IDDM.

12. A method according to claim 11, wherein said patient is tested for the presence of anti-hsp60 antibodies.

13. A method according to claim 12, wherein the test method comprises a radioimmunoassay.

14. A method according to claim 12, wherein the test method comprises an ELISA test.

15. A method according to claim 11, wherein said patient is tested for the presence of a T cell which immunoreacts with hsp60.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 573 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

```
Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Gly Trp Gly Ser Pro Lys Val Thr Lys Asp Gly Val Thr Val
65              70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320
```

```
Gly Gly Ala Val Phe Gly Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570

(2) INFORMATION FOR SEQ ID NO: 2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Val Leu Gly Gly Gly Val Ala Leu Leu Arg Val Ile Pro Ala Leu Asp
1               5                   10                  15

Ser Leu Thr Pro Ala Asn Glu Asp
            20

(2) INFORMATION FOR SEQ ID NO: 3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide
```

```
        (xi) SEQUENCE DESCRIPTION: SEQ ID NO: 3:

Glu Glu Ile Ala Gln Val Ala Thr Ile Ser Ala Asn Gly Asp Lys Asp
1               5                   10                  15

Ile Gly Asn Ile
            20

(2) INFORMATION FOR SEQ ID NO: 4:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 4:

Glu Gly Asp Glu Ala Thr Gly Ala Asn Ile Val Lys Val Ala Leu Glu
1               5                   10                  15

Ala (2) INFORMATION FOR SEQ ID NO: 5:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 5:

Ser Arg Leu Ser Lys Val Ala Pro Val Ile Lys Ala Arg Met Met Glu
1               5                   10                  15

Tyr Gly Thr Thr
            20

(2) INFORMATION FOR SEQ ID NO: 6:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Pro Gly Met Gly Ala Met Gly Gly Met Gly Gly Gly Met Gly Gly Gly
1               5                   10                  15

Met Phe
```